(12) United States Patent
Yigal et al.

(10) Patent No.: US 11,400,226 B2
(45) Date of Patent: Aug. 2, 2022

(54) INJECTOR PREMATURE ACTIVATION BLOCKING MECHANISM (71) Applicant: West Pharma. Services IL, Ltd., Ra'anana (IL)

(72) Inventors: Gil Yigal, Gan Yavne (IL); Yossi Bar-El, Beit Arye (IL)

(73) Assignee: WEST PHARMA. SERVICES IL, LTD., Ra'anana (IL)

( * ) Notice: Subject to any disclaimer, the term of this patent is extended or adjusted under 35 U.S.C. 154(b) by 256 days.

(21) Appl. No.: 16/636,168

(22) PCT Filed: Aug. 3, 2018

(86) PCT No.: PCT/US2018/045114
§ 371 (c)(1),
(2) Date: Feb. 3, 2020

(87) PCT Pub. No.: WO2019/032390
PCT Pub. Date: Feb. 14, 2019

(65) Prior Publication Data
US 2020/0368447 A1  Nov. 26, 2020

Related U.S. Application Data (60) Provisional application No. 62/543,897, filed on Aug. 10, 2017.

(51) Int. Cl.
*A61M 5/315* (2006.01)
*A61M 5/24* (2006.01)

(52) U.S. Cl.
CPC ...... *A61M 5/31535* (2013.01); *A61M 5/3158* (2013.01); *A61M 5/31501* (2013.01);
(Continued)

(58) Field of Classification Search
CPC ...... A61M 5/31571; A61M 2005/2414; A61M 2005/2496; A61M 2005/2403;
(Continued)

(56) References Cited

U.S. PATENT DOCUMENTS

2005/0075608 A1* 4/2005 Holdgate ............... A61M 5/24
604/151
2008/0108953 A1  5/2008 Moser et al.
(Continued)

FOREIGN PATENT DOCUMENTS

CN    102753233 A    10/2012
CN    105899248 A    8/2016
(Continued)

OTHER PUBLICATIONS

Int'l Search Report and Written Opinion dated Oct. 23, 2018 in Int'l Application No. PCT/US2018/045114.
Int'l Preliminary Report on Patentability dated Dec. 4, 2019 in Int'l Application No. PCT/US2018/045114.

*Primary Examiner* — Deanna K Hall
*Assistant Examiner* — Leah J Swanson
(74) *Attorney, Agent, or Firm* — BakerHostetler (57) ABSTRACT

An injector includes a housing and an activation button assembly movably mounted thereto and translatable from an unactuated position to an actuated position. A cartridge door is configured to receive therein a cartridge containing a substance to be dispensed, and is movably mounted to the injector housing between open and closed positions. A deflectable interference member is mounted within the injector housing and, in a resting position, blocks movement of the activation button assembly from the unactuated to the actuated position thereof. The activation button assembly is configured to activate the injector when in the actuated position, and is movable from the unactuated position to the actuated position solely upon deflection of the interference (Continued)

element out of the resting position thereof. The cartridge door, when in the closed position thereof and having the cartridge received therein, deflects the interference element out of the resting position thereof.

16 Claims, 5 Drawing Sheets (52) U.S. Cl.
CPC . *A61M 5/31571* (2013.01); *A61M 2005/2414* (2013.01); *A61M 2005/2496* (2013.01)

(58) Field of Classification Search
CPC ...... A61M 2005/2485; A61M 5/14248; A61M 2005/14268; A61M 2005/2407; A61M 2005/2411; A61M 2005/2492
See application file for complete search history.

(56) References Cited

U.S. PATENT DOCUMENTS

| | | |
|---|---|---|
| 2013/0211330 A1 | 8/2013 | Pedersen et al. |
| 2018/0154081 A1 | 6/2018 | Bar-El et al. |

FOREIGN PATENT DOCUMENTS

| | | | |
|---|---|---|---|
| JP | 2008-043761 A | 2/2008 | |
| JP | 2016-523123 A | 8/2016 | |
| WO | 2012032411 A2 | 3/2012 | |
| WO | WO-2012032411 A2 * | 3/2012 | .............. A61M 5/24 |
| WO | 2014144096 A1 | 9/2014 | |
| WO | WO-2017004315 A1 * | 1/2017 | .......... A61M 5/1452 |

\* cited by examiner

INJECTOR PREMATURE ACTIVATION BLOCKING MECHANISM

CROSS-REFERENCE TO RELATED APPLICATIONS

This application is a section 371 of International Application No. PCT/US2018/045114, filed Aug. 3, 2018, which was published on Feb. 14, 2019 under International Publication No. WO 2019/032390 A1, and which claims priority from U.S. Provisional Patent Application No. 62/543,897, titled "Activation Block Until Cartridge Fully Inserted", filed on Aug. 10, 2017, the entire contents of each of which are incorporated by reference herein.

BACKGROUND OF THE DISCLOSURE

The present disclosure is generally directed to an injector, and, more particularly, to a mechanism blocking premature injector activation.

An injector, such as, for example, a drug injector, is typically engaged with a user's skin to inject a substance, e.g., medicament, within a cartridge into the user. Improper activation, such as, for example, premature activation, of an injector may place a user at risk of not receiving the substance, or at least not receiving the proper dose of the substance. Conventionally, improper activation of an injector has been addressed after the activation has already occurred, by neutralizing the device. Such an approach is expensive, however, as the cartridge and the injector must then be replaced. Furthermore, replacement or re-purchase usually causes delay in administration of the substance, which may be time sensitive.

Therefore, it would be advantageous to manufacture an injector employing a premature activation blocking mechanism to prevent premature activation from occurring, rather than neutralize the injector after premature activation has already been performed.

BRIEF SUMMARY OF THE DISCLOSURE

Briefly stated, one aspect of the present disclosure is directed to an injector including an injector housing and an activation button assembly movably mounted to the injector housing. The activation button assembly is translatable from an unactuated position to an actuated position. A cartridge door is configured to receive therein a cartridge containing a substance to be dispensed, and is movably mounted to the injector housing between an open position and a closed position. A deflectable interference member is mounted within the injector housing, the deflectable interference member having a resting position blocking movement of the activation button assembly from the unactuated position thereof to the actuated position thereof. The activation button assembly is configured to activate the injector when in the actuated position. The activation button assembly is movable from the unactuated position to the actuated position solely upon deflection of the interference element out of the resting position thereof. The cartridge door, when in the closed position thereof and having the cartridge received therein, deflects the interference element out of the resting position thereof.

Another aspect of the present disclosure is directed to an injector including an injector housing and an injection needle translatable between a retracted position, wherein at least a tip of the injection needle is contained within the injector housing, and an injection position, wherein at least the tip of the injection needle protrudes from the injector housing. An activation button assembly is movably mounted to the injector housing and operatively connected to the injection needle. The activation button assembly is translatable from an unactuated position to an actuated position. A cartridge door is configured to receive therein a cartridge containing a substance to be dispensed, the cartridge door being pivotably mounted to the injector housing between an open position and a closed position. A deflectable cantilevered arm is mounted within the injector housing, the cantilevered arm having a resting position underlying at least a portion of the activation button assembly, thereby physically blocking movement of the activation button assembly from the unactuated position thereof to the actuated position thereof. The activation button assembly is configured to drive the injection needle into the injection position, when in the actuated position. The activation button assembly is movable from the unactuated position to the actuated position solely upon deflection of the cantilevered arm out of the resting position thereof. The cartridge door, when in the closed position thereof and having the cartridge received therein, deflects the interference element out of the resting position thereof.

BRIEF DESCRIPTION OF THE DRAWINGS

The following detailed description of aspects of the disclosure will be better understood when read in conjunction with the appended drawings. It should be understood, however, that the invention is not limited to the precise arrangements and instrumentalities shown. In the drawings.

DETAILED DESCRIPTION OF THE DISCLOSURE

Certain terminology is used in the following description for convenience only and is not limiting. The words "lower," "bottom," "upper" and "top" designate directions in the drawings to which reference is made. The words "inwardly," "outwardly," "upwardly" and "downwardly" refer to directions toward and away from, respectively, the geometric center of the injector, and designated parts thereof, in accordance with the present disclosure. Unless specifically set forth herein, the terms "a," "an" and "the" are not limited to one element, but instead should be read as meaning "at least one." The terminology includes the words noted above, derivatives thereof and words of similar import.

It should also be understood that the terms "about," "approximately," "generally," "substantially" and like terms, used herein when referring to a dimension or characteristic of a component of the invention, indicate that the described dimension/characteristic is not a strict boundary or parameter and does not exclude minor variations therefrom that are functionally similar. At a minimum, such references that include a numerical parameter would include variations that, using mathematical and industrial principles accepted in the art (e.g., rounding, measurement or other systematic errors, manufacturing tolerances, etc.), would not vary the least significant digit.

Referring to the drawings in detail, wherein like numerals indicate like elements throughout, there is shown in FIGS. 1-6 an injector, generally designated 10, in accordance with an embodiment of the present disclosure. In the illustrated embodiment, the injector 10 takes the form of a wearable injector (patch injector), such as, for example, without limitation, a wearable drug injector, but the disclosure is not so limited. As should be understood by those of ordinary skill in the art, the injector 10 generally includes a housing 12 having a first surface 14 configured to contact a skin surface of a user (not shown), e.g., a patient, the first surface 14 having an opening 14a therein. In the illustrated embodiment, the first surface 14 defines a base surface of the injector housing 12, but the disclosure is not so limited. The housing 12 also includes a second surface 16 opposing the first surface 14. In the illustrated embodiment, the second surface 16 defines a top, external surface of the injector housing 12, but the disclosure is not so limited.

Figure 2:
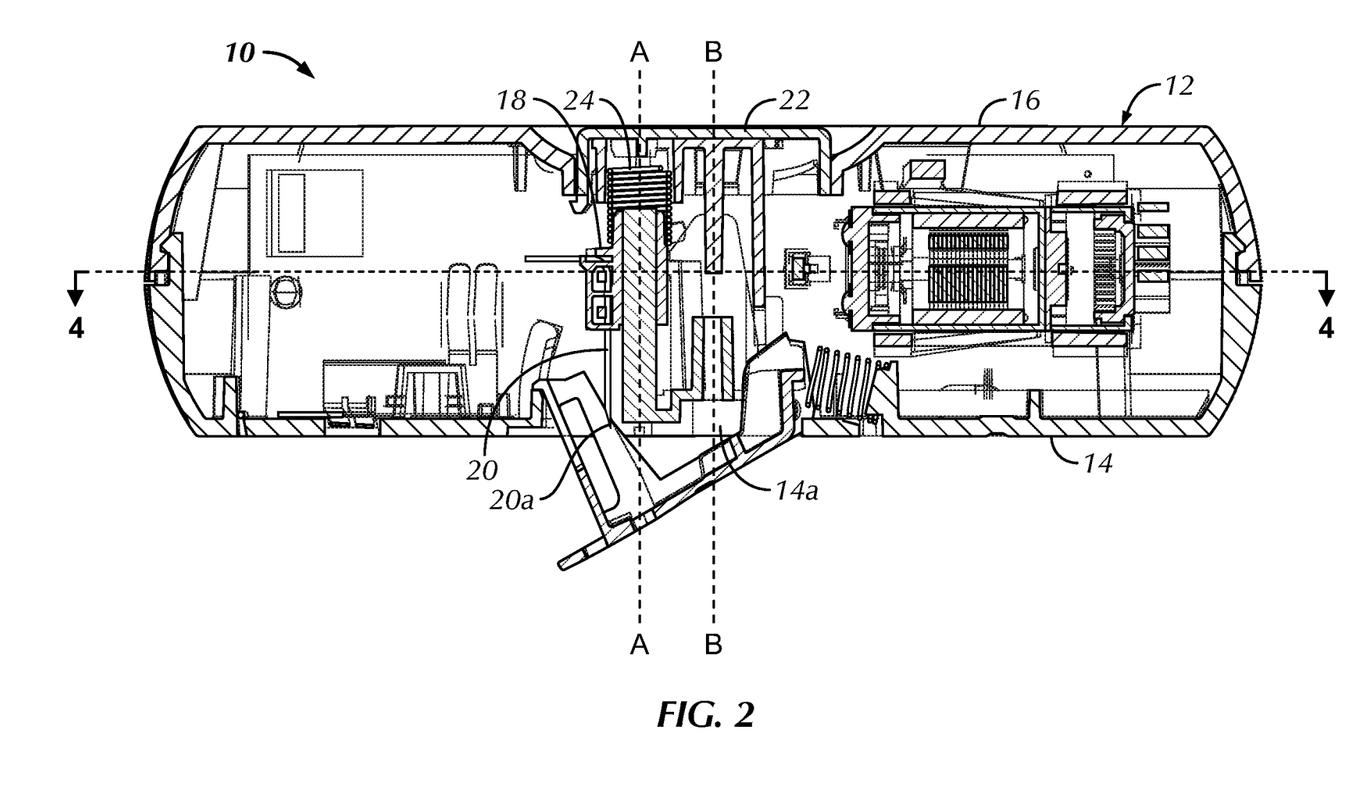
FIG. 2 is a cross-sectional view of the injector of FIG. 1, taken along the sectional line 2-2 of FIG. 1, with an activation button assembly in an unactuated position thereof and an injection needle in a retracted position thereof.
Figure 3:
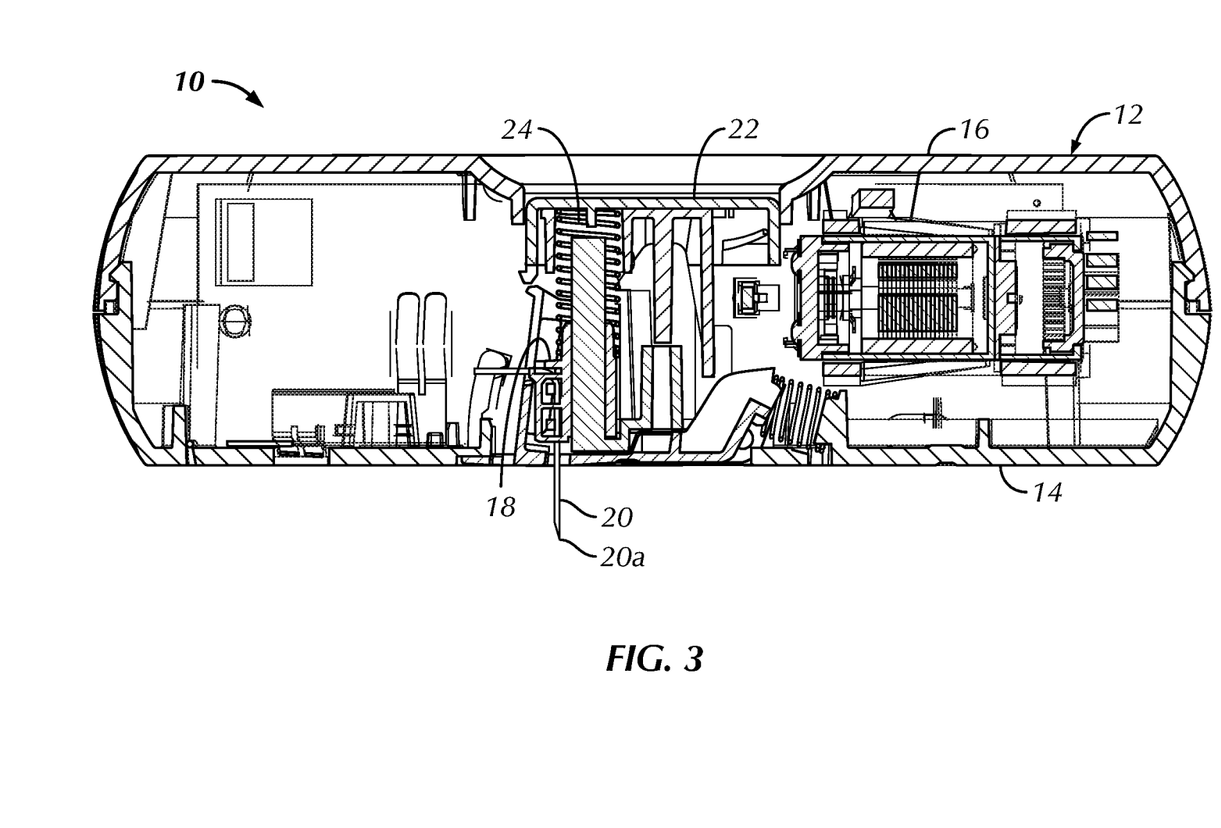
FIG. 3 is a cross-sectional view of the injector of FIG. 1, taken along the sectional line 2-2 of FIG. 1, with the activation button assembly in an actuated position thereof and the injection needle in an injection position thereof.

As shown in FIGS. 2-3, a needle hub 18, constructed, for example, from a polymeric or metal material, combinations thereof, or the like, is movably mounted within the injector housing 12 and an injection needle 20 is supported by the movable needle hub 18 in a manner well understood by those of ordinary skill in the art. In the illustrated embodiment, the needle hub 18 and the injection needle 20 are axially translatable along a needle axis A (FIGS. 2, 3) extending substantially perpendicularly to the first surface 14, between a retracted position (FIG. 2), wherein at least a tip 20a of the injection needle 20 is contained within the injector housing 12, and an injection position (FIG. 3), wherein at least the tip 20a of the injection needle 20 protrudes from the injector housing 12 through the opening 14a. As should be understood by those of ordinary skill in the art, however, the needle axis A may be positioned at angles other than 90° relative to the first surface 14. As also should be understood, the injection needle 20 may be movably mounted within the injector housing 12 via other mechanisms than the needle hub 18.

A depressible activation button assembly 22, constructed, for example, from a polymeric or metal material, combinations thereof, or the like, is movably mounted to the injector housing 12 and operatively connected to the injection needle 20. The activation button assembly 22 is translatable, i.e., depressible, along a button axis B from an unactuated position (FIGS. 1, 2) to an actuated position (FIG. 3) in a manner well understood by those of ordinary skill in the art, to activate the injector 10. In the illustrated embodiment, the button axis B is parallel to the needle axis A, but the disclosure is not so limited. Activation of the injector 10 includes, for example, driving the injection needle 20 from the retraction position to the injection position thereof.

As shown in FIGS. 2-3, a biasing member 24 is operatively connected with the activation button assembly 22 and the injection needle 20, but the disclosure is not so limited. As one alternative example, the biasing member 24 may be connected with the second surface 16 and the injection needle 20. The biasing member 24 is stabilized in a stored energy state in the unactuated position of the activation button assembly 22 (FIG. 2) and released into an energy releasing state, when the activation button assembly 22 is translated into the actuated position thereof (FIG. 3), to drive the injection needle 20 along the needle axis A from the retracted position thereof to the injection position thereof. As should be understood by those of ordinary skill in the art, the stored energy state of the biasing member 24 is a state in which the biasing member 24 stores at least some potential energy. The energy releasing state of the biasing member 24 is a state of the biasing member 24 in which the biasing member 24 releases at least some of the previously stored potential energy from the stored energy state.

In the illustrated embodiment, the biasing member 24 takes the form of a coil spring mounted between the needle hub 18 and the activation button assembly 22, i.e., the spring 24 abuts the activation button assembly 22 at one end and abuts the needle hub 18 at an opposing end. In the energy storing state, the coil spring 24 is at least partially compressed. In the energy releasing state, the coil spring 24 expands (relative to the at least partially compressed energy storing state) to drive the needle hub 18 and the injection needle 20 into the injection position thereof. As should be understood by those of ordinary skill in the art, however, the biasing member 24 may alternatively take the form of other members capable of storing and releasing energy. Non-limiting examples include other springs (e.g., torsion or leaf springs), elastic bands, and the like. Alternatively, the biasing member 24 may take the form of an actuator configured to apply a translational force onto the injection needle 20 when the activation button assembly 22 is depressed into the actuated position thereof.

The injector 10 further includes a cartridge door 26 defining an open end 26a for receiving, e.g., slidably, a cartridge 28 (FIGS. 4, 6) therethrough, and an interior channel 26b to receive the cartridge 28 therein. The interior channel 26b may be sized and shaped to receive and stabilize the cartridge 28 therein. Alternatively, the interior channel 26b may include a cartridge cradle, a cartridge track, individual stabilizing members, combinations thereof, or the like (not shown) to receive and stabilize the cartridge 28 in the interior channel 26b. As should be understood, the cartridge 28 contains a substance (not shown), e.g., medicament, to be dispensed from the injector 10 through the injection needle 20.

Figure 1:
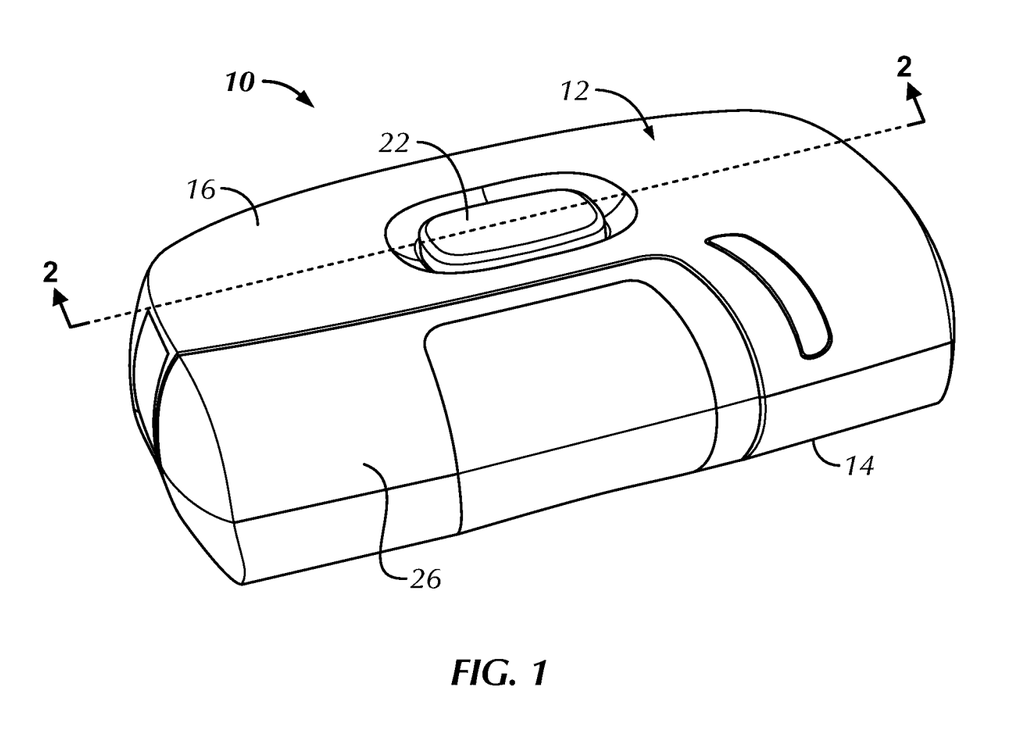
FIG. 1 is a top and front perspective view of a wearable injector, in accordance with an embodiment of the present disclosure.
Figure 4:
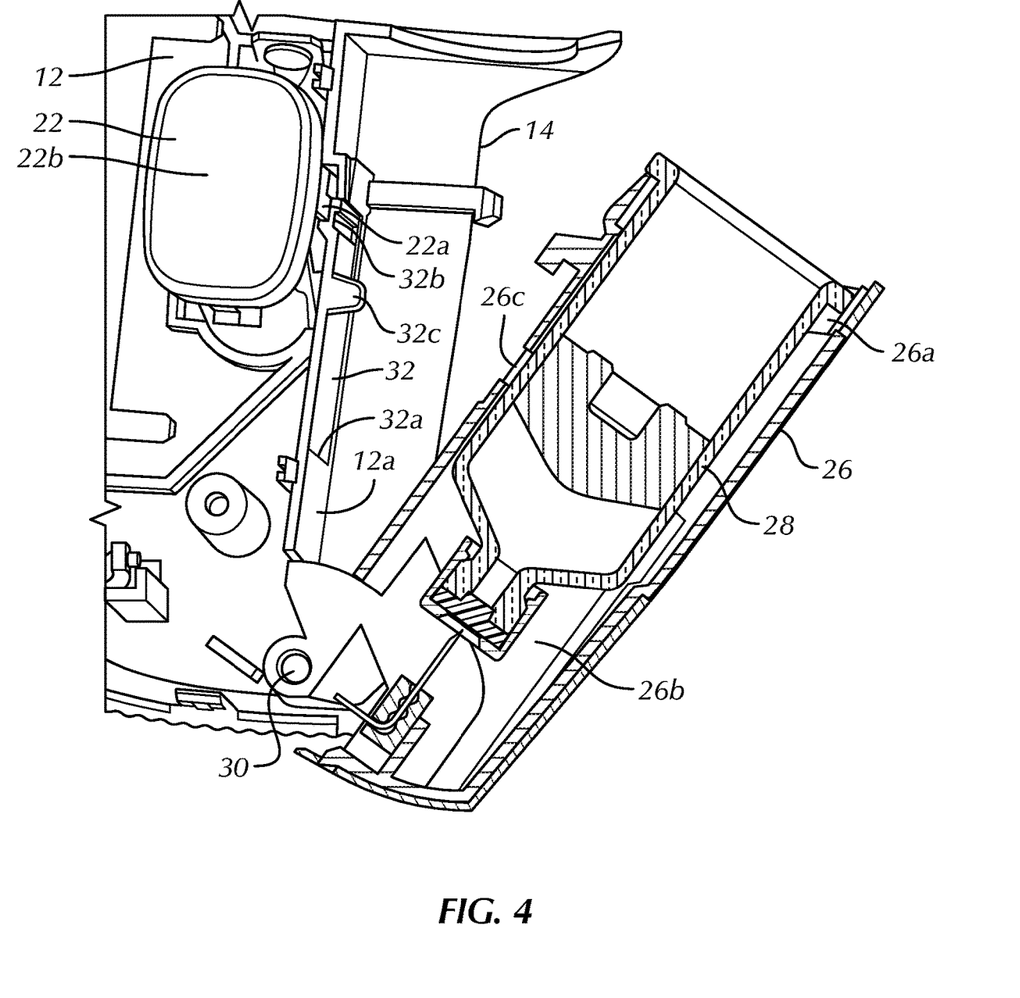
FIG. 4 is an enlarged, partial cross-sectional view of the injector of FIG. 1, taken along the sectional line 4-4 of FIG. 2, with a cartridge door of the injector in an open position thereof and a cartridge inserted therein.
Figure 5:
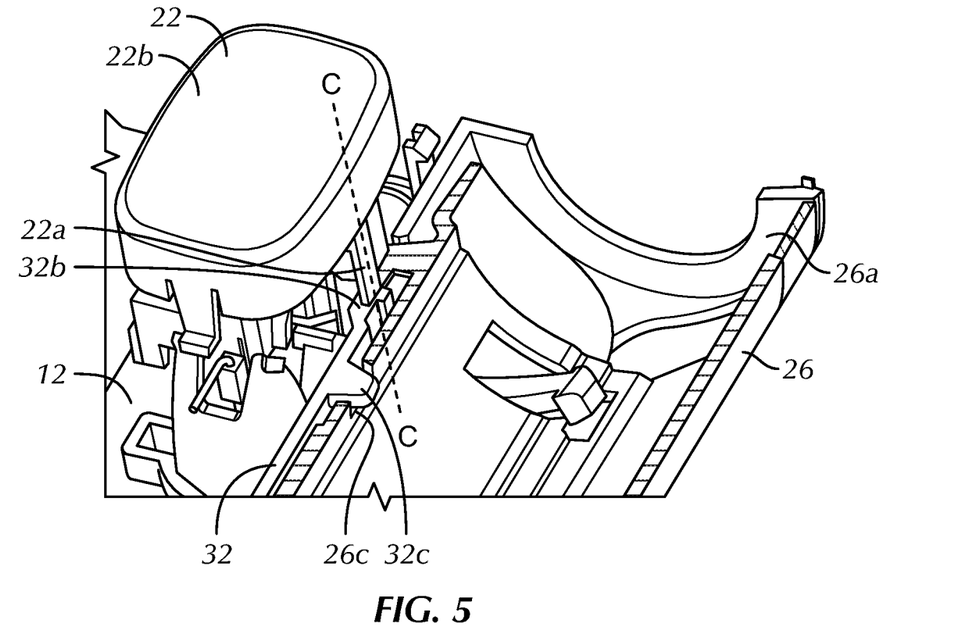
FIG. 5 is an enlarged, partial, perspective cross-sectional view of the injector of FIG. 1, taken along the sectional line 4-4 of FIG. 2, with the cartridge door of the injector in a closed position thereof without a cartridge inserted therein.
Figure 6:
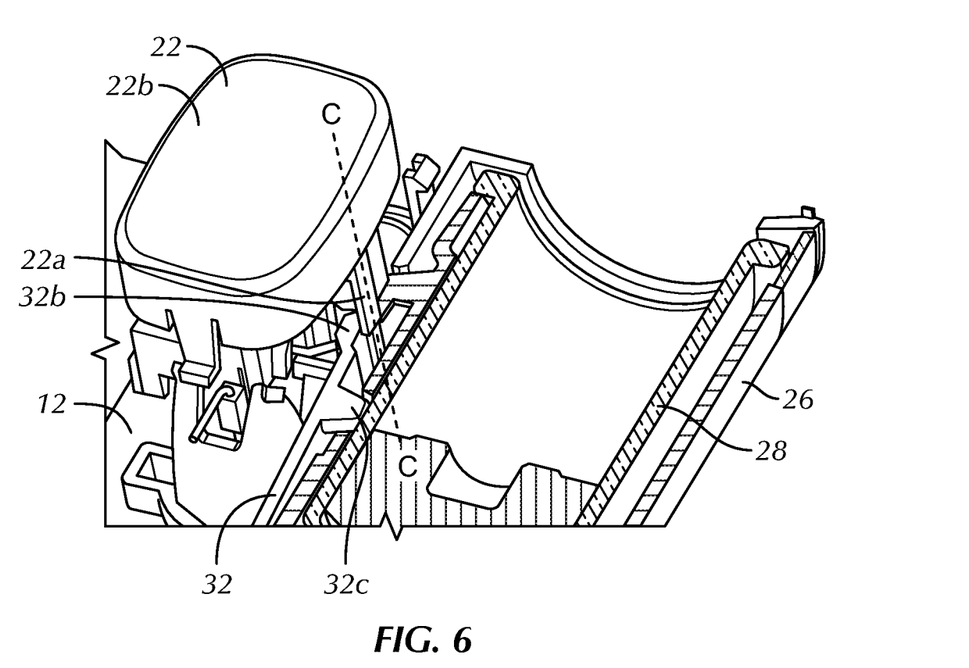
FIG. 6 is an enlarged, partial, perspective cross-sectional view of the injector of FIG. 1, taken along the sectional line 4-4 of FIG. 2, with the cartridge door of the injector in the closed position thereof with a cartridge inserted therein.

The cartridge door 26 is movably mounted to the injector housing 12, between an open position (e.g., FIG. 4) and a closed position (FIGS. 1, 5, 6). In the closed position, the interior channel 26b is inaccessible from outside the injector housing 12. For example, in the illustrated embodiment, the open end 26a of the cartridge door 26 is sufficiently covered by a portion of the injector housing 12 (see FIG. 1) such that access to the interior channel 26b is prevented. In the open position, the open end 26a of the cartridge door 26 is at least partially uncovered, and the interior channel 26b is at least partially accessible from the open end 26a. In a fully open position of the cartridge door 26, as shown in FIG. 4, the open end 26a of the cartridge door 26 is sufficiently uncovered to permit insertion of the cartridge 28 therethrough and into the interior channel 26b.

In the illustrated embodiment, the cartridge door 26 is pivotably attached to the injector housing 12, e.g., via pin connection 30, but the disclosure is not so limited. As shown in FIG. 4, the cartridge door 26 is pivoted away from the injector housing 12 in the open position, whereby the interior channel 26b is accessible from the open end 26a of the cartridge door 26. Other non-limiting examples of a cartridge door 26 movably mounted to an injector housing 12 are described in U.S. patent application Ser. No. 15/575,229, entitled, "Cartridge Insertion For Drug Delivery Device," the entire contents of which are incorporated by reference herein.

A deflectable interference member 32 is mounted within the injector housing 12. In the illustrated embodiment, the interference member 32 is positioned between the cartridge door 26 and the activation button assembly 22. As shown best in FIG. 4, the interference member 32 takes the form of a cantilevered arm. In one embodiment, the cantilevered arm 32 extends directly from the injector housing 12, but the disclosure is not so limited. In one embodiment, the cantilevered arm 32 is formed integrally with the injector housing 12, e.g., co-molded therewith, but the disclosure is not so limited. That is, the cantilevered arm 32 may be formed separately or individually and connected or attached, directly or indirectly to the injector housing 12.

In the illustrated embodiment, the injector housing 12 includes an elongate wall 12a projecting substantially perpendicularly from the first surface 14, between the cartridge door 26 and the activation button assembly 22. As should be understood by those of ordinary skill in the art, however, the wall 12a may be positioned at angles other than 90° relative to the first surface 14 and may be tapered, curved, or the like. The cantilevered arm 32 defines a deflectable portion of the wall 12a and extends therefrom, from a first end 32a of the cantilevered arm to a second, free end 32b of the cantilevered arm 32. That is, the first end 32a is attached to the wall 12a and defines a fulcrum about which the cantilevered arm 32 may be deflected. For example, without limitation, the first end 32a may define a living hinge about which the cantilevered arm 32 may be deflected. The deflectable cantilevered arm 32 may be constructed, for example, from a polymeric or metal material, a combination thereof, or the like. As should be understood by those of ordinary skill in the art, the cantilevered arm 32 may be deflectable due to material properties, dimensional properties, or a combination thereof. The cantilevered arm 32 is normally positioned in a resting position, substantially undeflected from the wall 12a.

In the resting position, the cantilevered arm 32 blocks movement of the activation button assembly 22 from the unactuated position thereof to the actuated position thereof along the button axis B. For example, the activation button assembly 22 includes a post 22a extending therefrom. In the illustrated embodiment, the post 22a extends downwardly (i.e., parallel with button axis B) from a cover 22b of the activation button assembly, but the disclosure is not so limited. The post 22a defines a post pathway C, parallel to the button axis B, along which the post 22a travels during movement of the activation button assembly 22 from the unactuated position to the actuated position. As shown in FIGS. 4 and 5, a portion of the cantilevered arm 32 intersects the post pathway C in the resting position thereof. In one embodiment, for example, the second, free end 32b of the cantilevered arm 32 may be positioned in the post pathway C in the resting position of the cantilevered arm 32, but the disclosure is not so limited. Accordingly, in the resting position, the cantilevered arm 32 abuts the post 22a so as to physically block travel of the post 22a along the post pathway C, and, therefore, the cantilevered arm 32 blocks movement of the activation button assembly 22 from the unactuated position thereof to the actuated position thereof.

As shown in FIGS. 4-6, the cartridge door 26 further includes a window 26c in a sidewall thereof. As should be understood, the window 26c may alternatively take the form of an opening or void permitting access therethrough to accomplish the same functions as described in further detail below. The window 26c is positioned in a portion of the sidewall of the cartridge door 26 facing the cantilevered arm 32. The window 26c permits access to the interior channel 26b of the cartridge door 26 therethrough. The cantilevered arm 32 includes a corresponding tab 32c projecting therefrom in a direction toward the window 26c. The tab 32c of the cantilevered arm 32 is positioned to align, and project through, the window 26c of the cartridge door 26, and into the interior channel 26b thereof in the closed position of the cartridge door 26. In the illustrated embodiment, the tab 32c projects laterally from the cantilevered arm 32, generally parallel to the first surface 14, but the disclosure is not so limited.

Upon movement of the cartridge door 26 to the closed position thereof, without a cartridge 28 inserted therein (as shown in FIG. 5), the tab 32c projects through the window 26c and into the interior channel 26b of the cartridge door, without leading to a change in the position of the cantilevered arm 32 from the resting position thereof. Conversely, upon movement of the cartridge door 26 to the closed position thereof, after a cartridge 28 has been inserted therein (as shown in FIG. 6), the tab 32c projects through the window 26c and engages the cartridge 28. Contact with the cartridge 28, however, stops the tab 32c from projecting further into the occupied interior channel 26b, but rather deflects the tab 32c and, in turn, deflects the cantilevered arm 32 out of the resting position thereof to a deflected position thereof (FIG. 6).

Deflection of the cantilevered arm 32 out of the resting position thereof moves the cantilevered arm 32 laterally out of the post pathway C (e.g., moves the second, free end 32b out of the post pathway C in FIG. 6), thereby unblocking and permitting the activation button assembly 22 to be moved from the unactuated position thereof to the actuated position thereof. Advantageously, therefore, the activation button assembly 22 is prevented from moving from the unactuated position thereof to the actuated position thereof either when the cartridge door 26 is in the open position thereof or if the cartridge door 26 is moved into the closed position thereof without a cartridge 28 loaded therein. Thus, the activation button assembly 22 is disabled from being prematurely actuated, and the injector 10 is disabled from being prematurely activated. The cantilevered arm 32 is deflected out of the resting position thereof only when a cartridge 28 is inserted into the interior channel 26b of the cartridge door 26 and the cartridge door 26 is moved to the closed position thereof. Advantageously, therefore, the activation button assembly 22 is movable into the actuated position thereof, only when the injector 10 is ready for activation, i.e., when the cartridge 28 is loaded and the cartridge door 26 is closed. Further advantageously, this mechanical premature activation blocking mechanism avoids sensors or the like, thereby avoiding incorporating additional, more complex components capable of failure. Yet further advantageously, engagement of the tab 32c with the cartridge 28, upon cartridge door 26 closure, may serve as an additional cartridge 28 stabilizing mechanism in the interior channel 26b.

It will be appreciated by those skilled in the art that changes could be made to the embodiments described above without departing from the broad inventive concept thereof. As one example, the injector may include a linkage between the activation button assembly 22 and the needle hub 18, the linkage being disconnected until a cartridge 28 is inserted into the cartridge door 26 and the cartridge door 26 is moved into the closed position thereof. Movement of the activation button assembly 22 while the linkage is disconnected nevertheless prevents activation of the device. Alternatively, or additionally, the activation button assembly may be secured in a depressed, non-activated state until the cartridge 28 has been inserted into the cartridge door 26 and the cartridge door 26 is moved into the closed position thereof. When the cartridge 28 is inserted, the activation button assembly 22 may be linked to the needle hub 18 and/or pop up, permitting a user to depress the button assembly 22. As another example, the interference element 32 may alternatively take the form of a sensor and/or an electronic switch, capable of performing the functions of the interference element 32 described herein. It is understood, therefore, that this invention is not limited to the particular embodiments disclosed, but it is intended to cover modifications within the spirit and scope of the present invention, as set forth in the appended claims.

We claim:

1. An injector comprising:
   an injector housing with a first surface and an elongate wall extending from the first surface;
   an activation button assembly movably mounted to the injector housing, the activation button assembly being translatable from an unactuated position to an actuated position;
   a cartridge door configured to receive therein a cartridge containing a substance to be dispensed, the cartridge door being movably mounted to the injector housing between an open position and a closed position; and
   a deflectable interference member with a first end connected to the elongate wall, a second end configured to engage with the activation button assembly, and a body between the first end and the second end, the body defining a deflectable portion of the elongate wall, the deflectable interference member positioned between the activation button assembly and the cartridge door and having a resting position blocking movement of the activation button assembly from the unactuated position thereof to the actuated position thereof,
   wherein:
   the activation button assembly is configured to activate the injector when in the actuated position,
   the activation button assembly is movable from the unactuated position to the actuated position upon deflection of the deflectable interference member out of the resting position thereof, and
   the cartridge door, when in the closed position thereof and having the cartridge received therein, deflects the deflectable interference member out of the resting position thereof.

2. The injector of claim 1, wherein the deflectable interference member comprises a cantilevered arm.

3. The injector of claim 2, wherein the cantilevered arm extends from the injector housing from the first end to the second end.

4. The injector of claim 2, wherein the activation button assembly comprises a post extending therefrom, the post having a post pathway along which the post travels from the unactuated position of the activation button assembly to the actuated position of the activation button assembly, and wherein the cantilevered arm, in the resting position thereof, is positioned in the post pathway, thereby physically blocking travel of the post, and, in turn, the activation button assembly from the unactuated position to the actuated position.

5. The injector of claim 4, wherein the second end is a free end positioned in the post pathway in the resting position of the cantilevered arm.

6. The injector of claim 2, wherein the cartridge door comprises a window in a sidewall thereof, the window facing the cantilevered arm, and wherein the cantilevered arm includes a corresponding tab projecting therefrom in a direction toward the window, the tab being configured to project through the window and into the cartridge door in the closed position of the cartridge door.

7. The injector of claim 6, wherein the tab is aligned with the window in the closed position of the cartridge door, and configured to project through the window in the closed position of the cartridge door and deflect upon engagement with the cartridge received within the cartridge door, to, in turn, deflect the cantilevered arm out of the resting position thereof.

8. The injector of claim 1, further comprising:
   an injection needle translatable between a retracted position, in which at least a tip of the injection needle is contained within the injector housing, and an injection position, in which at least the tip of the injection needle protrudes from the injector housing,
   wherein the activation button assembly is operatively connected to the injection needle, and activating the injector comprises driving the injection needle into the injection position.

9. The injector of claim 1, wherein the cartridge door is pivotably mounted to the injector housing.

10. An injector comprising:
    an injector housing with a first surface and an elongate wall extending from the first surface;
    an injection needle translatable between a retracted position, in which at least a tip of the injection needle is contained within the injector housing, and an injection position, in which at least the tip of the injection needle protrudes from the injector housing;
    an activation button assembly movably mounted to the injector housing and operatively connected to the injection needle, the activation button assembly being translatable from an unactuated position to an actuated position;
    a cartridge door configured to receive therein a cartridge containing a substance to be dispensed, the cartridge door being pivotably mounted to the injector housing between an open position and a closed position; and
    a deflectable cantilevered arm with a first end connected to the elongate wall, a second end configured to engage with the activation button assembly, and a body between the first end and the second end, the body defining a deflectable portion of the elongate wall, the cantilevered arm positioned between the activation button assembly and the cartridge door and having a resting position underlying at least a portion of the activation button assembly, thereby physically blocking movement of the activation button assembly from the unactuated position thereof to the actuated position thereof, wherein:

the activation button assembly is configured to drive the injection needle into the injection position, when in the actuated position, the activation button assembly is movable from the unactuated position to the actuated position upon deflection of the cantilevered arm out of the resting position thereof, and the cartridge door, when in the closed position thereof and having the cartridge received therein, deflects the cantilevered arm out of the resting position thereof.

11. The injector of claim 10, wherein the activation button assembly comprises a post extending therefrom, the post having a post pathway along which the post travels from the unactuated position of the activation button assembly to the actuated position of the activation button assembly, and wherein the cantilevered arm, in the resting position thereof, is positioned in the post pathway, thereby blocking travel of the post, and, in turn, the activation button assembly from the unactuated position to the actuated position.

12. The injector of claim 11, wherein the the second end is a free end positioned in the post pathway in the resting position of the cantilevered arm.

13. The injector of claim 11, wherein the cartridge door comprises a window in a sidewall thereof, the window facing the cantilevered arm, and wherein the cantilevered arm includes a corresponding tab projecting therefrom in a direction toward the window, the tab being configured to project through the window and into the cartridge door in the closed position of the cartridge door.

14. The injector of claim 13, wherein the tab is aligned with the window in the closed position of the cartridge door, and configured to project through the window in the closed position of the cartridge door and deflect upon engagement with the cartridge received within the cartridge door, to, in turn, deflect the cantilevered arm out of the resting position thereof.

15. The injector of claim 1, wherein the elongate wall extends substantially perpendicularly from the first surface.

16. The injector of claim 10, wherein the elongate wall extends substantially perpendicularly from the first surface.

* * * * *